United States Patent [19]

Entwistle et al.

[11] Patent Number: 4,520,007

[45] Date of Patent: May 28, 1985

[54] ANTI-COAGULANTS OF THE 4-HYDROXYCOUMARIN TYPE AND RODENTICIDAL COMPOSITIONS (BAITS) COMPRISING SUCH ANTI-COAGULANTS

[75] Inventors: Ian D. Entwistle, Sittingbourne; Peter Boehm, Maidstone, both of England

[73] Assignee: Shell Oil Company, Houston, Tex.

[21] Appl. No.: 504,348

[22] Filed: Jun. 14, 1983

[30] Foreign Application Priority Data

Jun. 14, 1982 [GB] United Kingdom ............... 8217219
Jan. 10, 1983 [GB] United Kingdom ............... 8300549

[51] Int. Cl.³ .................... A01N 43/16; A01N 25/08; A01N 25/00; C07D 311/56
[52] U.S. Cl. ...................... 424/17; 424/84; 514/822; 514/337; 514/457; 546/269; 549/285; 568/327; 568/306; 568/705; 568/808; 260/465 R; 260/465 F
[58] Field of Search ............. 549/285; 424/281, 84, 424/17

[56] References Cited

U.S. PATENT DOCUMENTS

3,764,693 10/1973 Boschetti et al. ............. 549/285
3,957,824 5/1976 Hadler et al. ............. 260/343.2 R
4,009,022 2/1977 Fujimoto ............. 71/93
4,035,505 7/1977 Hadler et al. ............. 424/281

OTHER PUBLICATIONS

B. Miller, J. Org. Chem., 42, (8), 1408–1415, (1977).
Hadler et al., *Nature*, 253, pp. 275–277, (1975).

*Primary Examiner*—Norma S. Milestone

[57] ABSTRACT

Compounds having blood-anticoagulant properties of the general molecular formula:

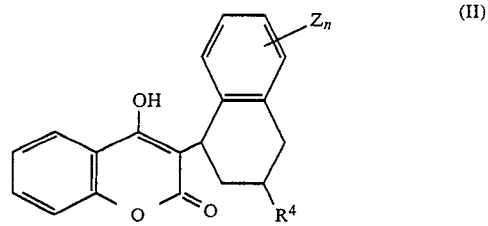

in which Z represents a halogen atom, preferably a chlorine atom, and n is 0, 1 or 2 and $R^4$ represents either (1) a grouping which comprises a phenylene radical attached directly or indirectly to the tetralin ring and having in the para position (with respect to such attachment) an electron-withdrawing atom or group whose rotational volume substantially does not exceed that of a phenyl group and which forms together with said phenylene radical a polarizable structure, or (2) a grouping selected from:

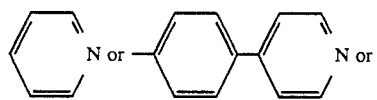

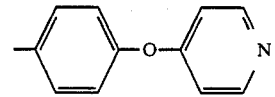

or (3) a grouping which comprises a phenylene radical attached directly to the tetralin ring and having in the para position (with respect to such attachment) a substituted furanyl or thiophenyl radical attached thereto directly or through oxygen and/or methylene, said furanyl or thiophenyl radical having such an electron-withdrawing atom or group as a substituent in a position forming with the furanyl or thiophenyl radical a polarizable structure, compounds of the type (1) in which $R^4$ contains two phenylene radicals linked essentially linearly by an aliphatic chain comprising a methylene radical or radicals and optionally at least one oxygen or sulphur atom being preferred.

Also included are the processes for the preparation of such compound; rodenticidal compositions containing them; and a method for controlling rodents by applying such a composition.

13 Claims, No Drawings

ANTI-COAGULANTS OF THE 4-HYDROXYCOUMARIN TYPE AND RODENTICIDAL COMPOSITIONS (BAITS) COMPRISING SUCH ANTI-COAGULANTS

The present invention concerns compounds useful as anti-coagulants. The invention also includes the preparation thereof. Such compounds include those of particular usefulness as rodenticides, and the invention also includes rodenticidal compositions (baits) in which anti-coagulant compounds in accordance with the present invention provide the, or the major, rodenticide component.

Anti-coagulants interfere with the blood coagulation mechanism, and their ability to do so depends on their chemical nature. Certain 4-hydroxycoumarin compounds of the general formula:

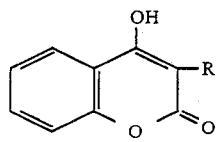 (I)

are known as having anti-coagulant properties and have been used successfully as a basis for rodenticides. Their rodenticidal activity depends on their anti-coagulant properties. The compound in which R in said formula is—CHPh—CH$_2$—CO—CH$_3$ is Warfarin, a well-known rodenticide. With the objective of providing additional 4-hydroxycoumarin compounds as a "second generation" alternative to Warfarin, U.S. Pat. No. 3,957,824 discloses certain rodenticidal 4-hydroxycoumarin compounds in which R in said formula signifies:

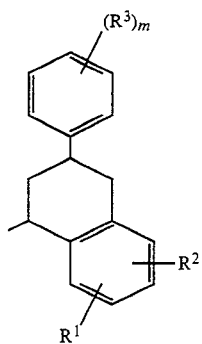

in which $R^1$ and $R^2$ are the same or different and are hydrogen or halogen atoms, preferably chlorine or bromine, or alkyl or alkoxy groups, preferably having up to 6 carbon atoms, $R^3$ is the same or different and is a halogen atom, a straight or branched chain alkyl or alkoxy group, preferably containing at least 2, more preferably from 5 to 12 carbon atoms, a cycloalkyl group, an aralkyl, preferably α-aralkyl group, a phenyl or phenoxy group, or a halogeno, preferably para halogeno, substituted derivative thereof, and m is 1 or 2.

U.S. Pat. No. 4,035,505 discloses rodenticidal compositions (baits) comprising a carrier in combination with a compound as just defined as the active ingredient.

Such 4-hydroxycoumarins, in particular those containing the diphenyl and p-bromo-diphenyl structure, which are known as Difenacoum and Brodifacoum respectively, have become commercially important for some time as the active ingredients, i.e. the rodenticides, of rodenticidal compositions effective against Warfarin-resistant rodents.

The most effective anticoagulant rodenticide of the prior art is Brodifacoum, which has a molecular structure in which $R_3$ of the above general formula comprises a para-bromo-phenyl radical. The structure thereof focusses attention on the essential presence of a halogen atom at the free end of the tetralin ring substituent, the halogen atom being attached to a benzene ring which itself is necessarily attached to the tetralin ring via a phenylene radical. In other words one sees a biphenyl structure with terminal halogen.

Brodifacoum is the most important commercial product for the control of rodents in view of its effectiveness against Warfarin-resistant rodents. (See MR. Hadler and R. S. Shadbolt, Nature, 253 (5489), 275, 1975).

The development of anticoagulant 4-hydroxy coumarin compounds has been limited to certain compounds of the general formulae above in which R represents a group containing a defined phenyl structure as in the original Warfarin or a defined biphenyl structure as in the later Difenacoum and Brodifacoum type compounds; and it is apparent from the prior art that the limitations in the permissible nature of the R group of the 4-hydroxy coumarin compounds hitherto found to have anticoagulant properties have been accepted in the art as defining two areas—and the only two areas, within which anticoagulant 4-hydroxy coumarin compounds can be found. In consequence, those in the art appear to have had no reason to consider that investigation outside those areas could be worthwhile, and the present Applicants are unaware of any prior publication concerning any such further investigation, or suggesting it might be worthwhile.

The Applicant worker's fundamental investigation into the relationship between structure and anticoagulant activity on which the present invention is predicated has surprisingly revealed other active compounds not disclosed in the prior art of which the at present preferred examples are those compounds in which instead of the biphenyl structure of $R^3$ there is a structure in which two phenylene radicals are linked together, in a para-para dash manner, by a linear radical as fully defined hereinafter and there is a terminal electron-withdrawing atom or group which confers a polarisable nature to the $R^3$ substituent, but with a bulk constraint in relation to that atom or group, and also in respect of the tetralin ring substituent as a whole, enabling the compound to act in an antocoagulant capacity. It has also been found that similar molecular characteristics, which the applicant workers have discovered to be important to the achievement of anticoagulant activity can be achieved in other ways than by the provision of two linked phenylene radicals, and the following broad definition of the compounds of the present invention accordingly includes compounds in which the tetralin ring substituent does not necessarily include two linked phenylene radicals.

The unexpected discovery of additional 4-hydroxy coumarin compounds was surprising and constitutes a valuable addition to the range of 4-hydroxy coumarin compounds currently available in the rodenticide art. Although in the hindsight knowledge of the present invention some of such compounds might be considered to have some structural similarity to the compounds of U.S. Pat. No. 3,957,824, there is nothing in the latter or in the general knowledge of the art to lead the expert to the compounds of the present invention.

According to the present invention there are provided compounds which have anticoagulant properties in relation to rats and which are of the general molecular formula:

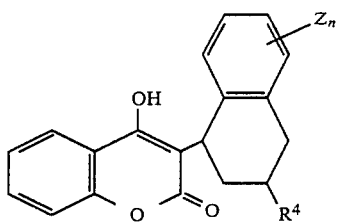

in which Z represents a halogen atom, preferably a chlorine atom, and n is 0, 1 or 2 and $R^4$ represents either (1) a grouping which comprises a phenylene radical attached directly or indirectly to the tetralin ring and having in the para position (with respect to such attachment) an electron-withdrawing atom or group whose rotational volume substantially does not exceed that of a phenyl group and which forms together with said phenylene radical a polarisable structure, or (2) a grouping selected from:

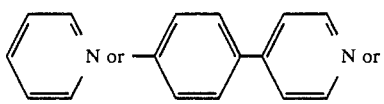

or (3) a grouping which comprises a phenylene radical attached directly to the tetralin ring and having in the para position (with respect to such attachment) a substituted furanyl or thiophenyl radical attached thereto directly or through oxygen and/or methylene, said furanyl or thiophenyl radical having an electron-withdrawing atom or group as a substituent in a position forming with the furanyl or thiophenyl radical a polarisable structure, said atom or group having a rotational volume which substantially does not exceed that of a phenyl group, Preferred compounds in accordance with the present invention are those in which $R^4$ represents a grouping (1) above, which includes a phenylene radical. When such phenylene radical is attached directly, or through another phenylene radical only, or through an oxygen atom and another phenylene radical, to the tetralin ring the electron-withdrawing atom or group should not be a halogen atom. Preferably, the just-stated preferred compounds are compounds in which the $R^4$ substituent in the tetralin ring contains two linked phenylene radicals, the outer one being attached to the para position of the inner one (itself attached in the para dash position to the tetralin ring) by a linear or essentially linear radical selected from: $-O-(CH_2)_m-$; $-(CH_2)_m-O-$; $-O-(CH_2)_m-O-$; $-(CH_2)_m-O-(CH_2)_p-$; $-(CH_2)_m-$; and the sulphur analogues thereof, in which m is 1 to 6 and p is 1 to 6. When said linking radical is $-(CH_2)_m-$, it is noted that such a radical represents the specific selection of a chain of from 1 to 6, preferably 2 to 4, more preferably 3, methylene radicals. This selection is not taught or evident from the prior art referred to herein; indeed the latter provides no indication that the general class of halo-substituted α-aralkyl group-substituted hydroxy coumarins arguably included in one of the general formulae disclosed therein were even prepared and examined for anticoagulant activity by the prior art workers. The inference is that such class of compounds were not of sufficient interest to examine in detail, and that the selected active compounds of the present invention in which m in the $-(CH_2)_m-$ is 1 to 6 remained unsuspected until the Applicant inventors' discovery. In so far as the compounds of the invention include those in which the electron-withdrawing group is other than a halogen atom, there is, of course, no disclosure or hint in the prior art referred to that such compounds are useful anticoagulants.

In addition to halogen atoms the following provides a list of electron-withdrawing groups X that came into consideration when preparing the compounds of the present invention as represented by general formula II above. Of these, the $-CN$ and $-CF_3$ groups are particularly preferred:

CN; $NO_2$; $SO_2R^5$; $CF_3$; $OCF_3$; $COOR^6$; $COR^7$; and (i)

(ii)

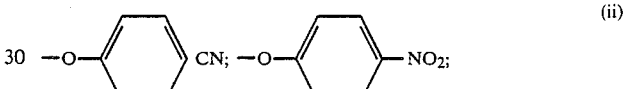

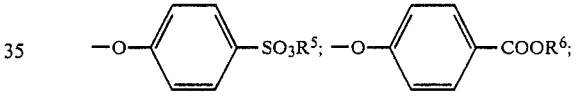

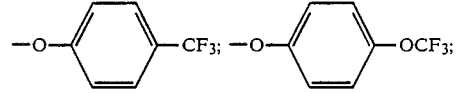

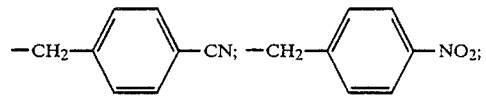

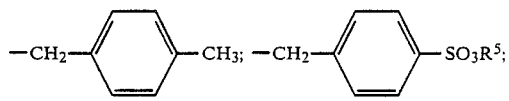

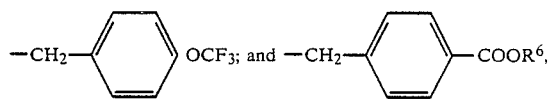

in which $R^5$, $R^6$ and $R^7$ signify alkyl groups. Examples of compounds in accordance with the invention are those in which $R^4$ is one of the following:

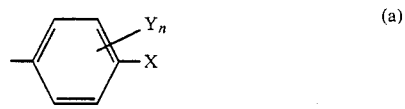

(a)

wherein X is as defined in (i) and (ii) above, but is preferably CN or $CF_3$, and n is 0, 1 or 2, providing that when n is 1 or 2, Y is fluorine or chlorine in a position adjacent to X.

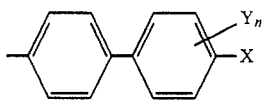
(b)

wherein X is as defined in (i) above, but is preferably CN or $CF_3$, and Y is fluorine or chlorine, and n is either 0, 1 or 2, providing that when n is 1 or 2, Y is in a position adjacent to X and X can also be a halogen atom.

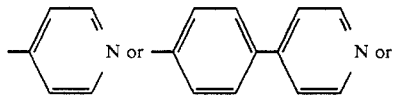
(c)

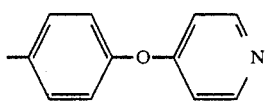

wherein X is as defined in (i) above, or is a halogen atom, preferably a bromine atom.

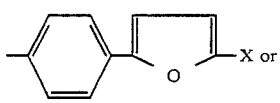

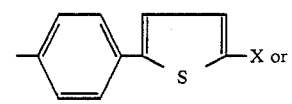

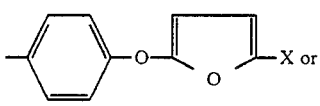

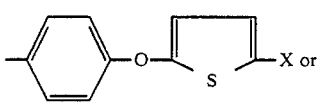

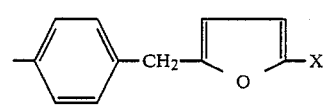

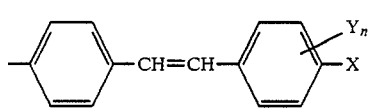
(e)

wherein X is as defined in (i) above and n=0, or is a halogen atom and Y is a halogen atom and n is 1 or 2.

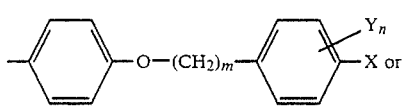
(f)

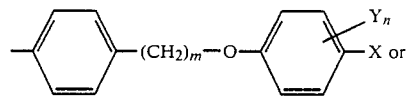

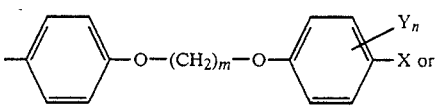

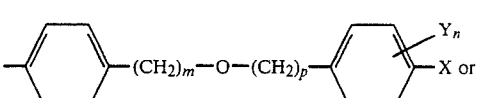

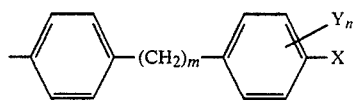

wherein X is as defined in (1) above and n=0, or is a halogen atom, Y is a halogen atom and n is 1 or 2; and m is 1 to 6 and p is 1 to 6, together with the sulphur analogues of the above structures in which an S atom replaces one or both O atoms.

Preferably the compounds of the present invention are all 4-hydroxy coumarin compounds of the general formula (I) in which the substituent R comprises a 3-substituted tetralin ring, the $R^4$ portion of which (see general formula II) is such that the compounds inhibit vitamin K and vitamin K 2, 3-epoxide reductases. It has recently been reported that Brodifacoum, Difenacoum and Warfarin have this inhibiting ability (See Fasco et al, J. Biol. Chem. 257, (19), 11210, 1982; Park et al, Biol. Pharmac., 31. (22), 3635, 1982), and, without wishing to be unduly limited by theoretical considerations, the present Applicants believe the molecular elongation of R measured via the 3-position and including $R^4$ advantageously should be such that substantially it does not exceed that of the phytyl side chain of vitamin K in order to inhibit the blood clotting process. As previously indicated certain molecular characteristics are required effectively to provide an inhibiting action in the compounds of the invention, namely a tetralin ring substituent $R^4$ which contains a structure of aromatic nature, ie. a phenylene ring or an equivalent heterocyclic ring structure, and which contains a terminal atom or group functioning as a soft electron-withdrawing group to provide a polarisable structure within the substituent $R^4$, the above-stated size constraint of $R^4$ (ie. a rotational volume substantially not exceeding that of a phenyl group) also being of importance in enabling the compound to block the blood clotting process.

The required binding ability is preferably achieved by providing within the grouping $R^4$ a polarisable (rather than an already polarised) structure involving an electron-withdrawing atom or group in the para position of a terminal phenylene radical, the required molecular elongation of R being achieved by attachment of that polarisable structure to the 3-position of the tetralin ring via a linear radical and a phenylene radical (which latter is directly attached to the tetralin ring), and the required size limitation, being achieved by avoiding the presence of meta and ortho substituents in the $R^4$ grouping, with the exception that a small halogen atom (fluorine or chlorine) is permissible in the meta position of the terminal phenylene radical.

Preferred compounds in accordance with the present invention are therefore those of the general formula II in which $R^4$ is the grouping:

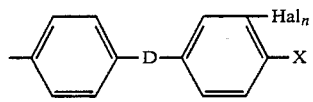

in which Hal is fluorine or chlorine and N=0 or 1, X is a soft electron-withdrawing atom or group, preferably a fluorine, chlorine or bromine atom or a CN or $CF_3$ group, and D represents $-CH=CH-$; or $-(A)_a-(B)_b-$; or $-(B)_b-(A)_a-$; or $-(A)_a-(B)_b-(A)_a-$, in which A is oxygen or sulphur and a is zero or a positive integer and B is $-CH_2-$ and b is zero or a positive integer, preferably 1 to 6, except when x is a halogen atom b is not zero. It will be understood that A and B can be linked in any order to form a chain of oxygen (or sulphur) atoms and methylene radicals, but preferably the compounds are those in which the chain is $-O-$ or $-O-(CH_2)_b-$ or $-(CH_2)_b-$. It will also be understood that advantageously the length of the chain comprising A and/or B substantially should not exceed in length that which provides a substituent R whose molecular elongation measured via the 3-position of the tetralin ring substantially does not exceed that of the phytyl side chain of vitamin K. All these structures have in common the ability to provide, in the 4-hydroxy coumarin compound molecule, a lipophilic group capable of exerting a binding action in relation to the blood clotting process. The discovery by the Applicant inventors of the two significant factors, namely the presence of a terminal "soft" electron-withdrawing group and a size limitation of the $R^4$ substituent in which that group is present, together with their discovery that the elongation of the $R^4$ grouping is susceptible of variation, but should be such that the elongation of R measured via the 3-position of the tetralin ring enables the required binding action to be exerted, has opened up a hitherto unsuspected area of anticoagulant 4-hydroxy coumarin compounds which is not predictable from a study of the prior art.

It appears from the Applicant's literature study that the prior patent specifications acknowledged earlier in this specification represent the only relevant prior art in respect of 4-hydroxy coumarin compound anticoagulants of the kind embodying a tetralin ring in their molecular structures, and the delay in finding of the additional and, in certain instances, more attractive (as rodenticides) anticoagulants of the present invention is surprising having regard to the extent to which the prior art compounds exemplified by Brodifacoum having become known and used in the art.

It is noted that in the general definition of anticoagulants in U.S. Pat. No. 4,035,505 there is reference to the possibility of the 3-substituent in the tetralin ring comprising a phenylene radical and, arguably, a halo-substituted terminal α-aralkyl group, but no examples thereof are provided, (the nearest example being a compound in which there is a non-halogenated terminal benzyl group). It would appear that the earlier workers failed to make such compounds, and that they certainly did not appreciate the need to select an alkyl chain in the terminal α-aralkyl group of terminal halo-substituted compounds whose length is such that the elongation of the R substituent measured via the 3-position of the tetralin ring enables the compound to inhibit the blood clotting process.

The inventor's researches have indicated that within the class of compounds of the present invention there is an appreciable difference between the activities of individual compounds. Some appear to be less active than the most active prior art compound, namely Brodifacoum. Although such less active compounds are, of course, useful, the Applicant is, of course, particularly interested in compounds having similar activity to, or better activity than, Brodifacoum, and a number of compounds in accordance with the invention which are of that nature have been made and tested. It would appear that in general there is a correlation between the specific structure and activity, and the indications are that among the factors of importance in that respect are an $R^4$ substituent in the 3-position of the tetralin ring in which there is (a) an aromatic ring attached to the tetralin ring and a terminal phenylene ring having an electron-withdrawing group in the para position, (b) a linear radical joining these two rings in a para/para dash relationship, the aromatic ring being attached to the tetralin ring in the para dash position, (c) the absence of side branchings and ortho or meta ring substituents, (d) an electron-withdrawing atom or group which is chlorine, bromine, CN, $CF_3$, $OCF_3$ or COR (where R is an alkyl, preferably methyl or ethyl, group), and (e) an overall elongation of the tetralin substructure measured via the 3-position of (and including the 2 and 3 position carbon atoms of) the tetralin ring, and including the $R^4$ substituent thereof, which is within a maximum beyond which the activity will decline. (As indicated above a maximum of the order of the distance to which the phytyl side chain of the vitamin K molecule extends provides a practical guide in this respect, and it appears desirable from the activity point of view to synthesise compounds in accordance with the invention which have overall elongation up to and preferably as near as possible to that maximum. However, greater elongations are not excluded and the extent to which it might be useful to make such compounds can readily be determined by routine toxicity testing on rodent species).

The present invention also includes rodenticidal compositions (baits) comprising a carrier in combination with, as active ingredient, a rodenticidally effective amount of a compound in accordance with the invention; and the invention also includes the method of exterminating rodents at a locus, or preventing or reducing loss or deterioration by rodent attach at said locus, by providing at said locus bait comprising a rodenticidal composition as just defined.

Such compositions can be formulated in accordance with procedures well-known per se in the art, and using any suitable bait base which constitutes an edible carrier. A convenient base is medium grade stabilised oatmeal, and the proportion of active ingredient incorporated therewith all depend on the inherent activity of the selected compound, which is readily determined by trial.

The compounds of the present invention can be prepared by a variety of synthesis routes employing reaction steps known per se, and using commercially available reactants or reactants which themselves can be readily synthesized. The detailed examples given hereinafter provide illustration of suitable synthesis chemistry.

Compounds of particular interest as anti-coagulant rodenticides are those of general formula:

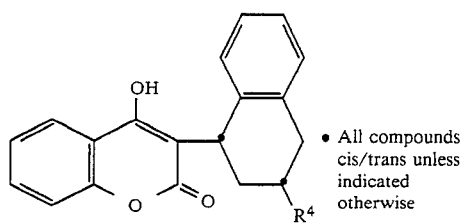

• All compounds cis/trans unless indicated otherwise in which $R^4$ is as indicated in the following table:

| Compound No. | $R^4$ |
|---|---|
| 1 | —C₆H₄—C₆H₄—CN (trans) |
| 2 | —C₆H₄—C₆H₄—CN (cis) |
| 3 | —C₆H₄—CF₃ |
| 5 | —C₆H₃(Cl)(Cl) (3,4-dichloro) |
| 6 | —CH₂—C₆H₃(Cl)(Cl) |
| 7 | —C₆H₄—CN |
| 8 | —(furan)—C₆H₄—Br |
| 9 | —C₆H₄—NO₂ |
| 10 | —C₆H₄—O—C₆H₄—CN |
| 11 | —C₆H₄—O—CH₂—C₆H₄—Br |
| 12 | —C₆H₄—OCH₂—C₆H₄—CN |
| 13 | —C₆H₄—OCH₂—C₆H₄—CF₃ |
| 15 | —C₆H₄—OCH₂—C₆H₄—F |
| 16 | —C₆H₄—OCH₂—C₆H₃(Cl)(Cl) |
| 17 | —C₆H₄—CH₂CH₂—C₆H₄—Br |
| 18 | —C₆H₄—CH₂CH₂—C₆H₄—Cl |
| 19 | —C₆H₄—CH₂CH₂—C₆H₄—CN |
| 20 | —C₆H₄—O—C₆H₄—CF₃ |
| 21 | —C₆H₄—CH=CH—C₆H₄—Br (t) |
| 22 | —C₆H₄—CH=CH—C₆H₄—H (t) |
| 23 | —C₆H₄—(CH₂)₃—C₆H₄—Cl |
| 24 | —C₆H₄—C₆H₄—CF₃ (trans) |
| 25 | —C₆H₄—C₆H₄—CF₃ (cis) |

The following is a detailed exemplification of the synthesis chemistry employed in preparing compounds in accordance with the present invention. One route thereto, referred to as Route A below, starts from the appropriate aldehyde.

Route A

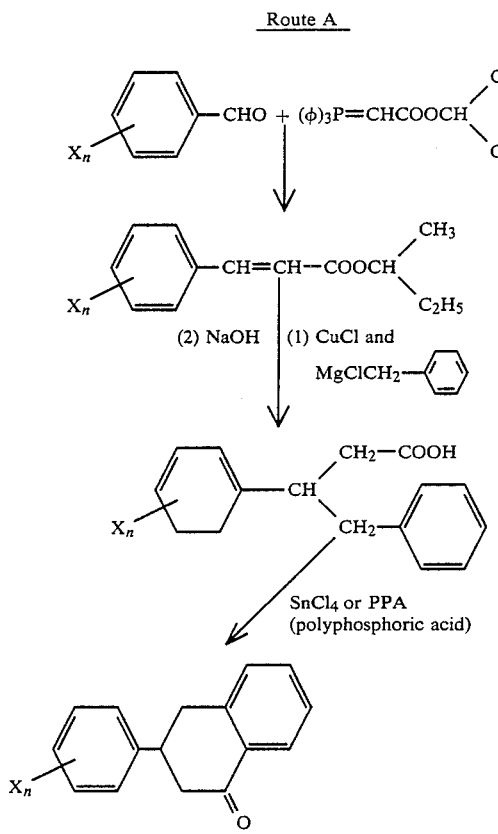

The resulting tetralones can then be reduced with NaBH₄ to the corresponding alcohols. This can be achieved at room temperature in ethanol solution. Compounds in accordance with the invention can be prepared from the alcohols by coupling the latter with 4-hydroxy coumarin, which can be achieved by heating at elevated temperature of the order of 160°–170° C. (Published literature of relevance in this respect is: R. S. Shadbolt, D. Woodward, P. J. Birchwood, J. C. S. (Perkins), 1190, 1976. J. s. Gillespie, S. P. Acharga, D. A. Shamblee, R. E. Davis, Tetrahedron, 31, 3, 1975. R. Sarges, J. Org. Chem., 40 (9), 1216, 1975).

When utilising Route A the benzaldehydes not available commercially will have to be synthesised, but this imposes no particular problems. For example, where appropriate one can employ the Sommelet reaction using hexamethylenetetramine; and for the preparation of the aldehyde precursor for compounds in accordance with the invention which contain furanyl rings eg. Compound 8 can utilise Vilsmeir formylation (phosphoryl chloride/dimethylformamide) of, for example, 1-bromo-4-furanyl benzene obtained by treatment of p-bromoaniline with NaNO₂/HCl followed by reaction with furan.

An alternative route (Route B hereinafter) which takes account of the sensitivity of the —CN group is referred to below. The starting compound can be prepared by the (Brodifacoum) synthesis chemistry of U.S. Pat. No. 3,957,824).

Route B

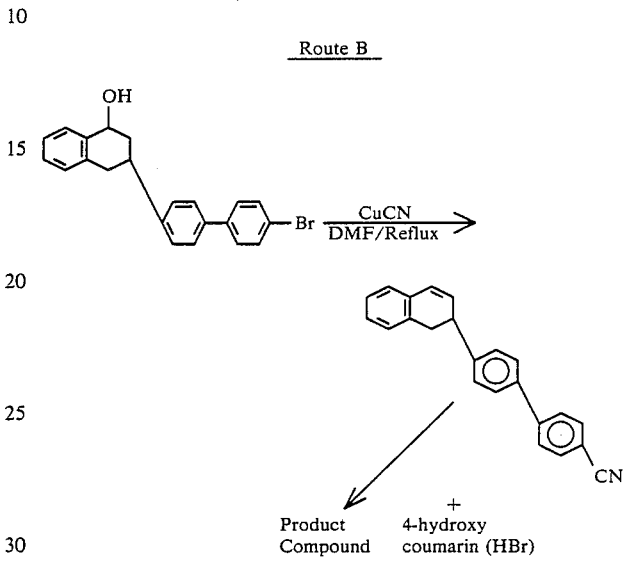

Product Compound + 4-hydroxy coumarin (HBr)

The product compound is prepared by coupling of the cyano-olefin with 4-hydroxy coumarin, and this is conveniently effected by the technique described UK Patent Specification 1,518,858. The alcohol starting material can be made by Route A. Alternatively, in a Modified Route B the starting material is the corresponding ketone, which is reacted with CuCN in dimethyl formamide (DMF) at eg. 160° C. to form the corresponding cyano-tetralone, eg.

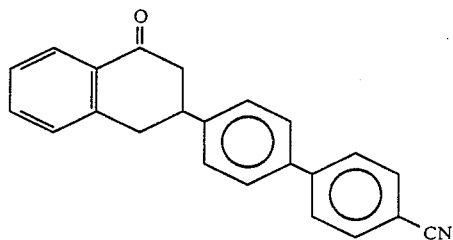

which is then reduced to the alcohol, which later is coupled with 4-hydroxy coumarin to form the desired product compound (as in Route C).

The following Route D to the tetralones is of interest for the preparation of the NO₂-substituted compounds, in which the sensitivity of the NO₂ group has to be taken into account:

Route C

-continued

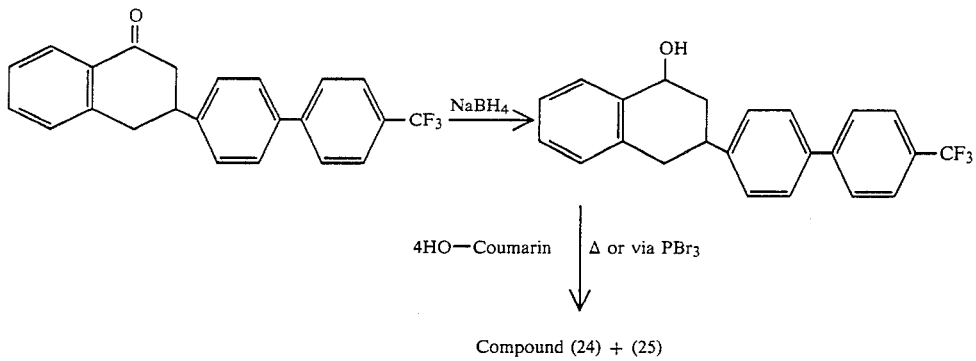

Compound (24) + (25)

ROUTE D

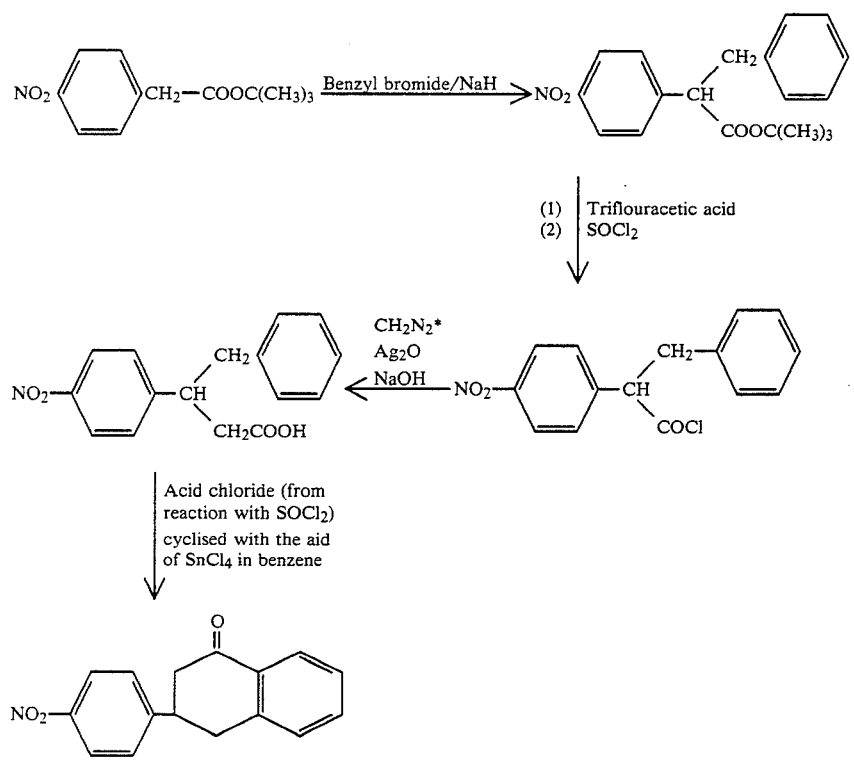

*Arnt-Eistert procedure (see Dann et al, Liebig Ann. Chem. 760, 67, Prep 19, 1972)

Thereafter the preparation follows the reduction and condensation (with 4-hydroxy coumarin) steps of Route C.

The above syntheses are exemplified by the preparation of the following compounds.

COMPOUNDS 1 AND 2

Preparation was effected by Route B and resolution into the cis and trans isomers by chromatography, the above-described Modified Route B also being used for Compound 1 preparation.

COMPOUNDS 3, 5 AND 6

Preparation was effected by Route A.

COMPOUND 7

This was made from p-bromobenzaldehyde by a combination of Routes A and and B.

COMPOUND 8

This was prepared by Route A, initially starting from p-bromoaniline from which the aldehyde

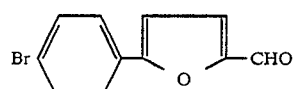

required for Synthetic Route A was prepared.

COMPOUND 9

This was prepared by Route D.

COMPOUND 10

This was prepared from anisaldehyde using Route A to the tetralone:

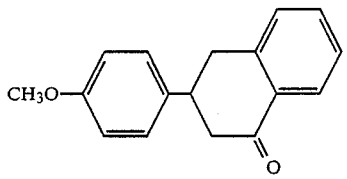

which, after demethylation to the hydroxy tetralone by heating under reflux with HBr, was then reacted with

to form the derivative:

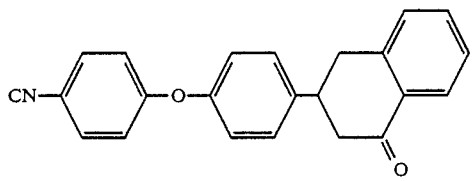

Thereafter the preparation followed the reduction and condensation (with 4-hydroxy coumarin) steps of Route A as exemplified in Route C.

COMPOUND 11

This was also prepared from anisaldehyde as for Compound 10, the hydroxy tetralone being reacted with

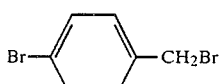

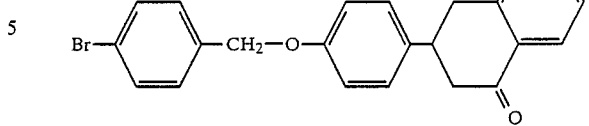

Thereafter the preparation followed the reduction and condensation steps of Route A.

COMPOUNDS 12 TO 16

These were obtained via a modification of Route A in which a tetralol intermediate was formed by Route A and then alkylated with the appropriate benzyl halide by stirring the potassium salt with the benzyl halide in DMF at ambient temperature. The desired alkylation products were readily isolated by crystallisation of the the crude product. In the case of Compound 12, the para-cyano group was introduced by using 4-bromo benzyl bromide as the benzyl halide reactant and then heating the resulting intermediate with CuCN in DMF.

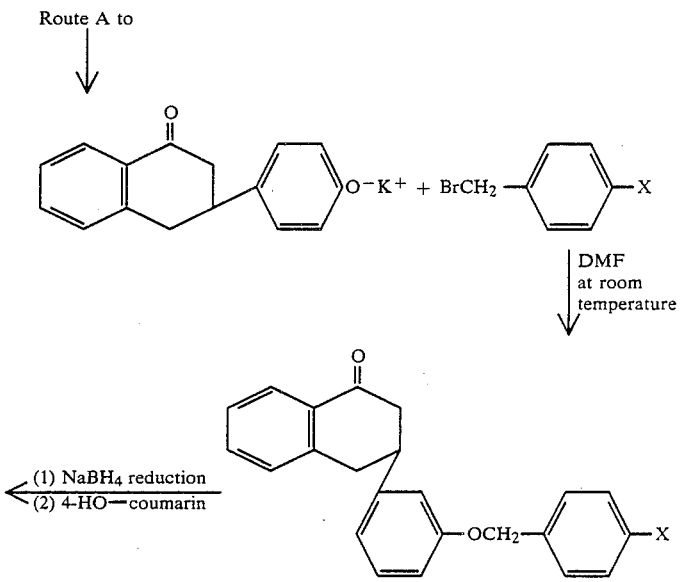

The ultimate ketone was converted into the required 4-hydroxy coumarin compound by reduction and condensation with 4-hydroxy coumarin as in Route A (as exemplified in Route C).

COMPOUNDS 17 TO 19

The key intermediate ketones required for these compounds were obtained using similar chemistry to that employed for Brodifacoum preparation as described in U.S. Pat. No. 3,957,824.

COMPOUND 20

This was prepared by Route A using the Sommelet route to the starting aldehyde.

COMPOUNDS 21 AND 22

These were obtained by Route A using the Wittig and Sommelet reactions to prepare the starting aldehyde. It is noted that in Compound 22 the

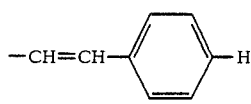

moiety is considered to provide a para-positioned electron-withdrawing group.

COMPOUND 23 TO 25

The starting hydrocarbon for the preparation of Compound 23 by Brodifacoum process chemistry was obtained by reaction of an acid chloride with the appropriate cadmium compound as follows (see K. M. Patel et al, Tett. Letters, 45, 4015, 1976):

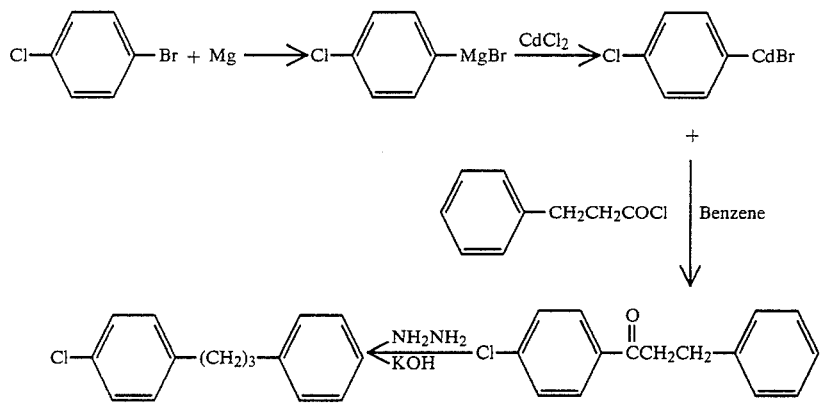

Compounds 24 and 25 were prepared by Route A, the starting aldehyde being made by heating the lithium salt of p-bromo-p'-trifluoromethyl biphenyl in DMF.

BIOLOGICAL TESTING

Compounds in accordance with the invention, and other substituted 4-hydroxy coumarin compounds not within the invention, including Brodifacoum, Difenacoum and Warfarin, were tested as described in the following examples. The Prothrombin time $ED_{50}$ value is the most reliable method for measuring anticoagulant activity. The $LD_{50}$ value is of significance in regard to the potency of the compound as a rodenticide.

From the results obtained it is clear that the new area of compounds discovered by the Applicant's invention represents a significant class of anticoagulants whose existence has hitherto been unsuspected, which includes compounds more active than Brodifacoum and many more active than Difenacoum.

The comparative data provided by compounds outside the invention which have been tested is relevant for the support it provides for the Applicant's selection of the characterising features referred to earlier which define the area of 4-hydroxy coumarin compounds of the invention. In particular reference is made to the following compounds:

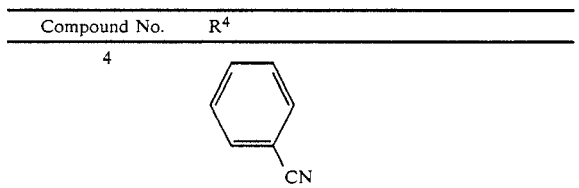

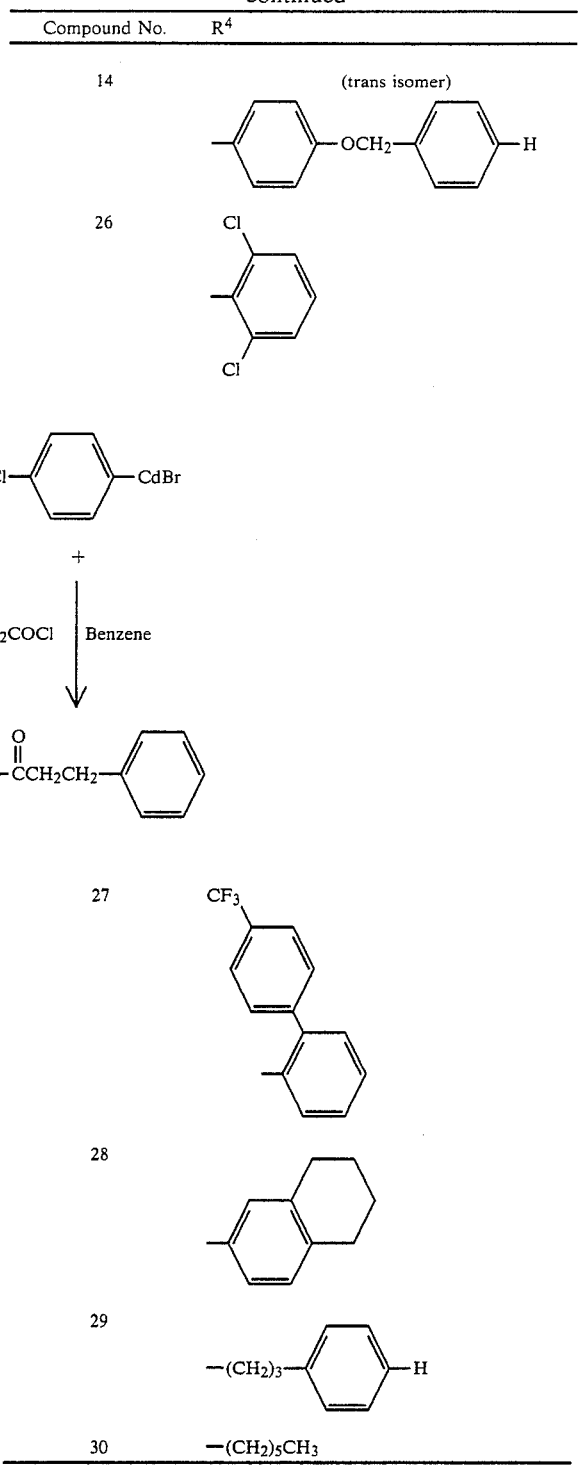

Compound 14 gave unexpected results on testing since it returned an activity much lower than similarly structured Difenacourm, which also has no para electron-withdrawing group. This is probably a biological effect, but since compound 14 is not a compound within the scope of the invention further work on that aspect would be of academic interest only.

Clear indications are apparent of the advantages of (1) a terminal para substituent in the $R^4$ substituent in the 3-position of the tetralin ring, which is a "soft"

electron withdrawing atom or group, eg—CF$_3$; (2) an R$^4$ substituent which comprises two phenylene radicals attached in the para-para dash positions and advantageously attached via a linear aliphatic chain; and (3) the absence of "bulk" in the R$^4$ substituent as would arise when its volume is increased by ortho or meta substituents and/or a non-linear configuration of that aliphatic chain. (It is at present believed that only the relatively small increase in bulk which would arise with say a small, eg methyl, side chain substituent or, as in Compound 16, a small terminal meta substituent can be regarded as permissible).

EXAMPLE I

The following Table II includes test data on compounds in accordance with the invention which was obtained in the following manner, together with similarly obtained comparative data.

A preliminary test was carried out to reliably rank the potential rodenticides in order of anticogulant potency.

The method used involved measurement of the Prothrombin time (a measure of blood clotting properties) which is based on that described in a paper by Quick, A. J., Stanley-Brown, M. and Bankoft. F. W. entitled "Study of Coagulation Defect in Haemophilia and in Jaundice" in American Journal of Medical Science, Vol. 190, pages 501–511, 1935. The compounds were dissolved in a 1:9 v/v mixture of triethanolamine and polyethylene glycol 200 Mol Wt and serially diluted to give appropriate doses in 1 ml per 1 kg of animal body weight. The doses were injected into the test animals by the interperitoneal route. Three days after injection, blood was withdrawn by cardiac puncture whilst the test animals (200–250 g Wistar strain male rats) were held under "Halothane" anaesthesia.

Three rats were used in each test of a given compound, and three prothrombin time determinations were carried out on each blood sample. Prothrombin times were determined using the modified one-stage method of Quick. The percentage extension time of each prothrombin time was determined by assigning 0% extension time to an arbitary prothrombin resting time of 12 seconds, and 100% extension time to a prothrombin time elevated to an arbitrary 212 seconds. Results were plotted on log-probability graph paper, the best-line fitted, and the prothrombin the ED50 read from the graph.

LD$_{50}$ data has also been obtained in respect of at least some of the compounds, and is included in Table II. The LD$_{50}$ figures for male Wistar rats were obtained in conventional manner by giving the rats various oral dose levels and applying regression analysis to the results in order to obtain the dose level for 50% deaths.

TABLE II

| Compound No | 3-day ED$_{50}$ mg/kg | LD$_{50}$ |
|---|---|---|
| 1 | 0.45 | 0.68 |
| 2 | 0.31 | 0.68 |
| 3 | 0.59 | 0.68 |
| 5 | 0.71 | — |
| 6 | 1.80 | — |
| 7 | 0.54 | 6.8 |
| 8 | 0.78 | — |
| 9 | 0.80 | — |
| 10 | 0.41 | 1.00 |
| 11 | 0.27 | 1.00 |
| 12 | 0.80 | — |
| 13 | 0.32 | 0.46 |
| 15 | 0.47 | — |
| 16 | 0.43 | — |
| 17 | 0.37 | 0.82 |
| 18 | 0.27 | 0.68 |
| 19 | 0.90 | — |
| 20 | 0.23 | 0.32 |
| 21 | 0.80 | — |
| 22 | 0.80 | — |
| 23 | 0.23 | — |
| 24 | 0.47 | — |
| 25 | 0.46 | — |
| Comparative data | | |
| Brodifacoum | 0.28 | 0.27 |
| Difenacoum | 0.56 | 1.80 |
| Warfarin | 5.2 | — |
| 4 | 7.0 | — |
| 14 | 4.3 | — |
| 26 | 10 | — |
| 27 | >>10.0 | — |
| 28 | 10.0 | — |
| 29 | 14.1 | — |
| 30 | 14 | — |

It will be apparent that of the prior art compounds only Brodifacoum appears to have particularly notable activity, Difenacoum having only about 36% of its activity. In the hindsight knowledge of the present inventor's discoveries, it might be concluded that the grouping:

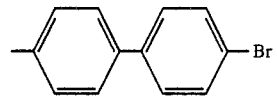

is of particular value when present as the R$^4$ substituent in the 3-position of the tetralin ring. This is, of course, a hindsight conjecture since, as indicated previously, the teachings in relation to the Brodifacoum type of anticoagulant (U.S. Pat. No. 3,957,824) provide no indication of this or hint of the possibility that the compounds of the present invention are likely to have anti-coagulant properties. Indeed the poor results obtained for compounds having apparent similarity to the compounds of U.S. Pat. No. 3,957,824 show clearly that without the teachings of the present invention, which indicate the additional area in which active compounds can be made (and which in hindsight may be said to provide some insight of why the prior published, limited area of U.S. Pat. No. 3,957,824 yielded active compounds), it is not possible to envisage from the prior art which compounds are going to be active and which are not, even assuming the average reader of U.S. Pat. No. 3,957,824 would conceive that other active compounds could exist despite the plainly specific nature of the prior patented area.

The present invention, however, provides not only a further, novel area of active 4-hydroxy coumarin compounds, but also compounds within that area which have an activity greater than Brodifacoum, for example, Compounds 11, 18, 20 and 23 above, in each of which there are not only the two phenylene radicals in the R$^4$ substituent, but these are joined together, and spaced apart by an oxygen atom or methylene radical or a chain thereof.

EXAMPLE II

Appropriate amounts of Compounds 1, and 3 and 5 were dissolved in acetone, serially diluted, and slurried onto rolled oats to give final bait concentrations of 5.0, 2.0, 0.5 and 0.2 ppm for Compound 1 and 20.0, 10.0, 0.5 and 2.0 ppm for Compounds 3 and 5. Each bait was offered as a 5 day no-choice feed to groups of five individually caged male rats, Wistar strain. The rats were observed for a further 21 days and deaths recorded.

| Compounds | BAIT CONCENTRATION ppm | DEATHS UP TO 21 DAYS |
| --- | --- | --- |
| 1 | 5.0 | 5/5 |
|  | 2.0 | 5/5 |
|  | 0.5 | 5/5 |
|  | 0.2 | 0/5 |
| 5 | 20.0 | 5/5 |
|  | 10.0 | 5/5 |
|  | 5.0 | 5/5 |
|  | 2.0 | 5/5 |
| 3 | 20.0 | 5/5 |
|  | 10.0 | 5/5 |
|  | 5.0 | 5/5 |
|  | 2.0 | 5/5 |

EXAMPLE III

Appropriate amounts of Compounds 1,2,3 and 5 were dissolved in acetone and slurried onto rolled oats to give final bait concentrations of 20 ppm for Compounds 1 and 2; and 50 ppm for Compounds 3 and 5. Each bait was offered as a 24h no-choice feed to groups of five individually caged female rats Homozygous—Resistant Welsh strain; and similarly to groups of five individually caged male and female mice (Cambridge Cream Resistant strain). The rats and mice were observed for a further 21 days and deaths recorded.

| COMPOUND | BAIT CONCENTRATION PPM | DEATH UP TO 21 DAYS RATS | MICE |
| --- | --- | --- | --- |
| 2 | 20.0 | 5/5 | 4/5 |
| 1 | 20.0 | 5/5 | 5/5 |
| 5 | 50.0 | 5/5 | 4/5 |
| 3 | 50.0 | 5/5 | 3/5 |

The following provides a more detailed description of the preparation of compounds referred to herein. Analyses and melting points in respect of Compounds 1-3, 5, 7-13 and 15-25 are given in the table at the end of this description.

Route A

Compound 20

1. A mixture of 4(p-trifluoromethylphenoxy)benzaldehyde (30 g) and sec butyloxycarbonyl methylene triphenylphosphorane (50 g) dissolved in dichloromethane was allowed to stand for 1 hour at room temperature. After evaporation of the solvent the white solid was tritiated with petroleum ether to give a solution which on evaporation yielded sec butyl 4-(p-trifluoromethylphenoxy)cinnamate (40 g) b.p. 150°/0.007 mm.

Required: C 65.9; H, 5.2; F, 15.6 for $C_{20}H_{19}O_3F_3$. Found: C, 66.1; H, 5.5.

2. A solution of sec Butyl 4-p-trifluoromethylphenoxy)cinnamate (35 g) in diethylether (200 ml) was added dropwise over 0.5 hr to 9 stirred solution of benzyl magnesium chloride (from 30 g of benzylchloride in 500 ml diethylether) containing 100 mg of CuCl. A saturated solution of ammonium chloride was added and the ether extracts washed with water, dried (MgSO4) and evaporated to give sec butyl 3-(4(p-trifluoromethylphenoxy)phenyl)-4-phenylbutyrate (25 g) b.p. 180°/0.007 mm.

Required: C, 71.0; H, 5.9; F, 12.5 for $C_{27}H_{27}O_3F_3$. Found: C, 70.9; H, 6.0.

3. A mixture of sec butyl 3-(4(p-trifluoromethylphenoxy)phenyl)-4-phenyl butyrate (25 g) and aqueous potassium hydroxide (21 g) in ethanol was refluxed for six hours. After evaporation of the solution to low volume water was added and the solution extracted with ether. The ether extracts were discarded and the aqueous solution acidified. Ether extraction then yielded a white solid characterised as 3-(4(p-trifluoromethylphenoxy)phenyl)-4-phenyl butyric acid (23 g) m.p. 74–75.

Required: C, 69.0; H, 4.7; F, 14.2 for $C_{23}H_{19}O_3F_3$. Found: C, 68.6; H, 4.7.

4. 3-(4(p-trifluoromethylphenoxy)phenyl)-4-phenylbutyric acid (23 g) was refluxed in benzene with thionyl chloride (46 ml) for one hour. The solution was then evaporated to dryness and the residue dissolved in benzene (23 ml). A solution of stannic chloride (23 g) in benzene (46 ml) was added at 0° with stirring. The solution was allowed to stir at 0° for 0.5 hr. Ice; water, diethylether and dilute HCl were then added sequentially. The ether extracts were further washed with aqueous potassium hydroxide and evaporated to give 3-(4-(p-trifluoromethylphenoxy)phenyl)tetralone m.p. 136°–137° (ethanol).

Required: C, 72.2; H, 4.4; F, 14.9 for $C_{23}H_{17}O_2F_3$. Found: C, 71.6; H, 4.5.

Route B 1. 3-(4'-bromo-4-bi-phenyl)tetralin-1-ol (20 g) was refluxed in dimethylformamide (7 ml) with cuprous cyanide (5.45 g) for four hours. After cooling an aqueous solution of ferric chloride (21 g in 30 ml H2O) containing concentrated hydrochloric acid (5 ml) was added and the mixture heated to 60°–70° for 0.5 hr. The cooled mixture was extracted with dichloromethane to give a solid (18 g) which was purified by chromatography on silica gel with dichloromethane. A fraction (7.1 g) was identified as 3-(4'-cyano-4-biphenyl)-3,4-dihydronaphthalene, m.p. 137°–138°.

Required: C, 89.9; H, 5.6; N, 4.6 for $C_{23}H_{17}N$. Found: C, 90.4; H, 5.6; N, 4.6.

2. 3-(4'-bromo-4-biphenyl)tetralin-1-one (13 g) was similarly heated with CuCN to obtain 3-(4'-cyano-4-biphenyl)tetralin-1-one (9.3 g) m.p. 197°.

Required: C, 85.4; H, 5.3; N, 4.3 for $C_{23}H_{17}ON$. Found: C, 84.4; H, 5.1; N, 4.5.

This was then converted into a mixture of compounds (1) and (2) via reduction with NaBH4 and condensing with 4-hydroxycoumarin as in Route C.

Route C 1. 3-(4'-trifluoromethyl-4-biphenyl)tetralin-1-one (m.p. 132° (CH3OH), Required: C, 75.4; H, 4.7; F, 15.6 for $C_{23}H_{17}OF_3$; Found: C, 75.4; H, 4.8 (17 g) was dissolved in ethanol (350 ml). Sodium tetrahydroborate (2.1 g) was added portionwise to the solution and the mixture stirred at 30° C. for 1.5 hours. The solution was then reduced to low volume by evaporation under reduced pressure, water added and the mixture extracted with diethylether. Evaporation of the extracts gave a white solid, which was crystallised from acetonitrile to give 3-(4'-trifluoromethyl-4-biphenyl)tetralin-1-ol (10 g) m.p. 171°–172°.

Required: C, 75.0; H, 5.2; F, 15.5 for $C_{23}H_{19}OF_3$. Found: C, 74.3; H, 5.2.

2. Phosphorous tribromide (3.69) in dichloromethane was added dropwise to a solution of 3-(4'-trifluoromethyl-4-biphenyl)tetralin-1-ol (9 g) in dichloromethane (200 ml) at 0°–5° C. The mixture was stirred for 2 hrs at RT. Water was added and the separated dichloromethane solution was wasted with water and dried voer anhydrous magnesium sulphate. Evaporation gave an oil which was refluxed in glacial acetic acid (30 ml) with 4-hydroxycoumarin (8.1 g) for 3 hrs. Water was added to the cooled mixture which was then extracted with dichloromethane. The dichloromethane extracts were evaporated to give a solid which was chromatographed on a column of silica gel. Elution with dichloromethane gave fractions containing isomeric forms of 3[3-(4'-trifluoromethyl-4-yl)-1,2,3,4-tetrahydro-1-naphthyl]-4hydroxycoumarin. The first eluted isomer (compound 24 (trans) about the 1,3 positions of the tetrahydronaphthyl (0.89) m.p. 207.5°.

Required: C, 75.0; H, 4.5; F, 11.1 for $C_{23}H_{23}O_3F_3$. Found: C, 74.6; H, 4.6. Compound 25.

The second isomer (cis) 0.69 g was eluted following elution of a mixture of isomers (4.7 g) cis m.p. 212°.

Required: C, 75.0; H, 4.5; F, 11.1. Found: C, 73.8; H, 4.8.

A mixture of isomers is also obtained when the tetralin-1-ol was heated with an equimolar quantity of 4-hydroxy coumarin. These methods are described in detail in J.C.S. Perkin I. 1190 1976 by R. S. Shadbolt, D. R. Woodward and P. J. Birchwood.

Compound 8

1. A solution of sodium nitrite (200 g in 290 ml $H_2O$) was added to a solution of para bromoaniline (500 g) in dilute hydrochloric acid (conc. HCl 727 ml in 3150 ml water) at 5° C. The rate of addition was controlled so as to keep the reaction temperature <10°. After addition was completed the mixture was stirred for 1 hours at 3° C. A solution of zinc chloride (3969 in 1000 ml of water) was then added with stirring at room temperature. After stirring for a further 10 minutes the solid precipitate was filtered off and dried in a vacuum oven. The diazonium zinc chloride salt (688 g) was then used without further characterisation.

2. Powdered sodium hydroxide (49) and sodium acetate (40 g) were added over a period of 0.3 hr at 25° to a stirred suspension of the salt in (1) above in furan (600 ml). The mixture was stirred for 24 hrs. when it was diluted with water (200 ml) and the organic layer separated. The aqueous solution was extracted with diethyl ether and combined with the furan solution. The extracts were washed with water and dried over anhydrous magnesium sulphate. Evaporation of the extracts yielded a dark oil which was chromatographed on silica gel with dichloromethane. A fraction (32 g) was identified by N.M.R. to be 2(4-bromophenyl)furan.

3. (Vilsmeir procedure) Phosphorous oxychloride $POCL_3$ (12.5 g) and Dimethyl formamide (7 ml) were added to a mixture of 2(4-bromophenyl)furan (20.4 g) in chlorobenzene (100 ml). The mixture was stirred at 10° for one hour. A further addition of $POCl_3$ (1.5 g) and DMF (0.7 g) was then made and the reaction stirred for a further one hour at RT. The mixture was poured onto ice, neutralised with sodium carbonate and the precipitated solid crystalised from chloroform (119). This solid was chromatographed on silica gel in chloroform to give 2(4-bromophenyl)furural (11 g) m.p. 153.5°.

Required: C, 52.6; H, 2.3; Br, 31.8 for $C_{23}H_7O_2Br$. Found: C, 52.9; H, 2.5; Br, 31.3.

Route D

Compound 9

1. Sodium hydride (1.49) was added to a solution of t-butyl 4-nitrophenyl acetate (14 g) in dimethyl formamide. When evolution of hydrogen had ceased benzyl bromide (11 g) was added dropwise and the mixture stirred at room temperature overnight. Water was added and the mixture extracted with dichloromethane. Evaporation of the extracts gave a solid which crystallised from ethanol to give t-butyl 2-benzyl[4-nitrophenyl]acetate (8.5 g) m.p. 98°–99°, Required: C, 69.5; H, 6.7; N, 4.2 for $C_{19}H_{21}O_4N$. Found: C, 69.9; H, 6.4; N, 4.3.

2. The above ester (6 g) was stirred with trifluoroacetic acid in dichloromethane from 2 hours at room temperature. After evaporation the residue was crystallised to give 2-benzyl[4-nitrophenyl]acetic acid (4.8 g) m.p. 163°–164°.

Required: C, 66.4; H, 4.8; N, 5.2 for $C_{15}H_{13}NO_4$. Found: C, 66.1; H, 4; N, 5.

3. 2-Benzyl[4-nitrophenyl]acetic acid (4 g) was converted to 3(Nitrophenyl)-4-phenylbutyric acid (3.8 g) by the Arndt-Listert procedure described in Liebig. Ann. Chem. p. 67, 760, 1972. (Preparation 19). m.p. 136°–137°

Required: C, 67.4; H, 5.2; N, 4.9 for $C_{16}H_{15}NO_4$. Found: C, 67.2; H, 5.3; N, 5.0.

4. Conversion of 3(4-nitrophenyl)-4-phenylbutyric acid (7.5 g) to 3-(4-nitrophenyl)tetralin-1-one (4.5 g) m.p. 162°–163°; Required: C, 71.9; H, 4.8; N, 5.2 for $C_{16}H_{13}NO_3$; Found: C, 71.7; N, 4.8; N, 5.2; was carried out using conditions and quantity relationships as described for Route A.

Compound 10 3(4-methoxyphenyl)tetralin-1-one m.p. 94°–195°. Required: for $C_{17}H_{16}O_2C$, 80.9; H, 6.3. Found: C, 80.9; H, 6.4. (35 g) in glacial acetic acid (200 ml) was refluxed with 48% HBr (150 ml) for 4 hours. After cooling water was added and the precipitate filtered off and washed with ethanol to give 3(4-hydroxyphenyl)tetralin-1-one (28 g) m.p. 194°–195°.

Required: C, 80.6; H, 5.8 for $C_{16}H_{14}O_2$. Found: C, 80.6; H, 6.1.

Compounds 12 to 16

3(4-hydroxyphenyl)tetralin-1-one (7 g) and potassium t-butoxide (3.3 g) were mixed in t-butanol and the solution evaporated to dryness under reduced pressure at 70°. The solid was dissolved in dimethylformamide and 4-fluorobenzyl chloride (4 g) added. This mixture was stirred overnight at room temperature, then diluted with water and extracted with dichloromethane. Evaporation of the extracts gave a solid which crystalised from ethanol to give 3(p-fluorobenzyloxyphenyl)tetralin-1-one (2.3 g) m.p. 155°–156.

Required: C, 79.8; H, 5.5; F, 5.5 for $C_{23}H_{19}O_2F$. Found: C, 79.4; H, 5.7.

Compounds 17 and 18

The starting compounds being known compounds and conversion to the tetralone being carried out by "Brodifacoum chemistry" (as described in the cited U.S. Patent) further detailed description of the laboratory preparation thereof by the present inventors is considered unnecessary.

Compound 23

1. Phenylpropionyl chloride (33.7 g) in benzene was added dropwise to a stirred mixture of 4-chlorophenyl magnesium bromide (derived from 38 g of 4-chlorobromobenzene) and cadmium chloride (37 g) in benzene at 0°. The mixture was stirred at room temperature for 6 hours and aqueous ammonium chloride solution then added. Ether extraction yielded p-chlorophenyl phenylethyl ketone (25 g) m.p. 78°-79°.

Required: C, 73.6; H, 5.3; Cl, 14.5 for $C_{15}H_{13}OCl$. Found: C, 73.2; H, 5.1; Cl, 15.5.

2. p-chlorophenyl phenylethyl ketone (25 g) was refluxed with hydrazine hydrate (13 g) and potassium hydroxide (18 g) in Digol (diethylene glycol) for one hour. The mixture was then distilled until the solution temperature in the still reached 175°. The mixture was then refluxed for 3 hours, cooled, poured into water and extracted with petroleum ether (Bpt 40°-60°). Evaporation of the extracts gave 1-(4-chlorophenyl)-3-phenylpropane Bbt. $110°/10^{-3}$ mm.

Required: C, 78.1; H, 6.5 for $C_{15}H_{15}Cl$. Found: C, 78.3; H, 6.7.

Compounds 24 and 25

N-Butyllithium in hexane (95 ml, 1.55M) was added dropwise to 4-Bromo-4'-trifluoromethylbiphenyl (40 g) in 250 ml of THF under $N_2$ at −70° C. After addition the mixture was stirred for a further 10 mins and then dry dimethylformamide (19.49) in a solution of dry tetrahydrofuran (100 ml) was added dropwise. The mixture was then allowed to warm to room temperature in the absence of coolant. After stirring for 1.5 hours water was added and the mixture extracted with ether. The water washed and dried extracts were evaporated to give p-(4-trifluoromethylphenyl)benzaldehyde (34.5 g) m.p. 70°.

Required: C, 65.5; H, 3.8; F, 23.92 for $C_{14}H_9OF_3$. Found: C, 66.4; H, 3.7.

| Compound No | | Required | Found | M.P (°C.) |
|---|---|---|---|---|
| 1 | C | 81.8 | 81.2 | 214-215 |
|   | H | 4.9 | 5.1 | C/T |
|   | N | 3.0 | 2.7 | |
| 2 | | | | 249-250 |
| 3 | C | 71.5 | 71.0 | 172-173 |
|   | H | 4.4 | 4.2 | |
| 5 | C | 68.7 | 69.0 | 207-209 |
|   | H | 4.2 | 3.9 | (cis) |
|   | Cl | 16.2 | | |
| 7 | C | 79.4 | | 218-220 |
|   | H | 4.9 | | |
|   | N | 3.5 | | |
| 8 | C | 67.8 | 66.0 | 101-102 |
|   | H | 4.1 | 3.7 | |
|   | Br | 15.6 | | |
| 9 | C | 72.6 | 72.4 | trans 223-224 |
|   | H | 4.6 | 4.6 | cis 265-266 |
|   | N | 3.9 | 3.7 | |
| 10 | C | 79.2 | 79.2 | 187-188 |
|    | H | 4.8 | 4.9 | |
|    | N | 2.9 | 2.6 | |
| 11 | C | 69.4 | 69.1 | 173-174 |
|    | H | 4.5 | 4.5 | |
|    | Br | 14.4 | | |
| 12 | C | 79.3 | 78.9 | 207-208 |
|    | H | 5.0 | 5.0 | |
|    | N | 2.1 | 2.1 | |
| 13 | C | 73.0 | 72.1 | 85-86 |
|    | N | 4.6 | 4.4 | |
| 15 | C | 78.0 | 77.8 | 149-150 |
|    | H | 5.1 | 5.0 | |
| 16 | C | 70.7 | 70.6 | 95-96 |
|    | H | 4.4 | 4.5 | |
|    | Cl | 13.1 | | |

| Compound No | | Required | Found | M.P (°C.) |
|---|---|---|---|---|
| 17 | C | 71.9 | 71.3 | 105-106 |
|    | H | 4.9 | 4.6 | |
|    | Cl | 14.5 | | |
| 18 | C | 78.2 | 78.0 | 170-171 |
|    | H | 5.4 | 5.4 | |
|    | Cl | 7.0 | | |
| 19 | C | 82.1 | 81.4 | 109-110 |
|    | H | 5.5 | 5.4 | |
|    | N | 2.8 | 2.8 | |
| 20 | C | 72.6 | 73.1 | 107-108 |
|    | H | 4.5 | 4.4 | |
|    | F | 10.8 | | |
| 21 | C | 72.1 | 71.8 | 231-232 |
|    | H | 4.6 | 4.5 | |
|    | Br | 14.5 | | |
| 22 | C | 84.2 | 83.3 | 141-142 |
|    | H | 5.6 | 5.4 | |
| 23 | C | 78.4 | 78.1 | 66-67 |
|    | H | 5.6 | 5.6 | |
|    | Cl | 6.8 | | |
| 24 | C | 75.0 | 74.6 | 209-210 |
|    | H | 4.5 | 4.6 | |
|    | F | 2.4 | | |
| 25 | C | 75.0 | 73.8 | 212-213 |
|    | H | 4.5 | 4.8 | |
|    | F | 2.4 | | |
| (25 + 26) | C | 75.0 | 74.6 | |
|    | H | 4.5 | 4.6 | |
|    | F | 2.4 | | |

What is claimed is:

1. A compound of the formula II

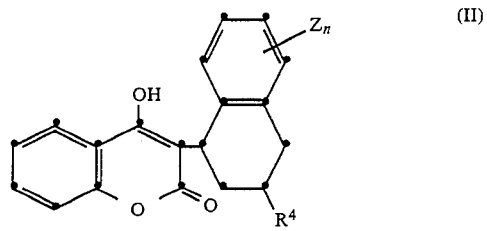

in which Z represents a chlorine atom, n is 0, 1 or 2 and $R^4$ represents

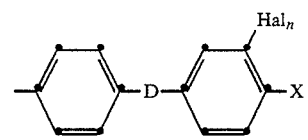

in which Hal is a fluorine or chlorine atom and n is 0 or 1, X is a fluorine, chlorine or bromine atom or a CN, $CF_3$ or $OCF_3$ group and D represents —$OCH_2$— or —$(CH_2)_m$—, where m is 2 to 3.

2. A compound according to claim 19 where each n is O, X is a bromine atom and D is O—$CH_2$—.

3. A compound according to claim 1 wherein each n is O, X is a chlorine atom and D is —$(CH_2)_m$— in which m is 2 or 3.

4. A compound according to claim 1 wherein each n is O, X is a bromine atom and D is —$(CH_2)_m$— in which m is 2.

5. A compound according to claim 19 wherein $Hal_n$ is a chlorine atom.

6. A compound according to claim 5 wherein n is $Z_n$ is O, X is a chlorine atom and D is —O—$OCH_2$—.

7. A compound of the molecular formula II

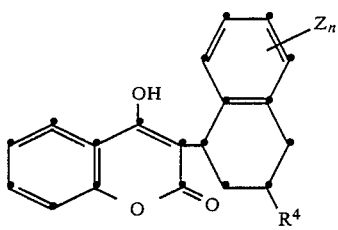
(II)

in which Z represents a chlorine atom, n is 0, 1 or 2 and $R^4$ represents

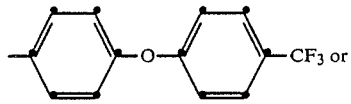

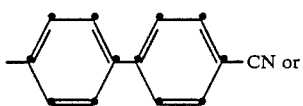

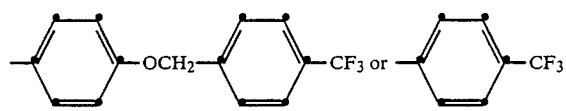

the compound being in cis or trans or mixed cis/trans form.

8. A compound according to claim 7 wherein n is 0 and $R^4$ represents

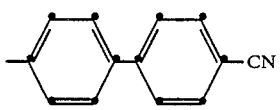

9. A compound according to claim 7 wherein n is 0 and $R^4$ represents

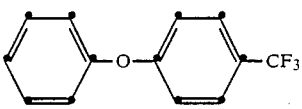

10. A compound according to claim 7 wherein n is 0 and $R^4$ represents

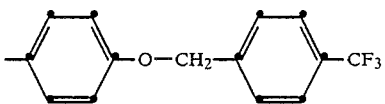

11. A compound of the formula

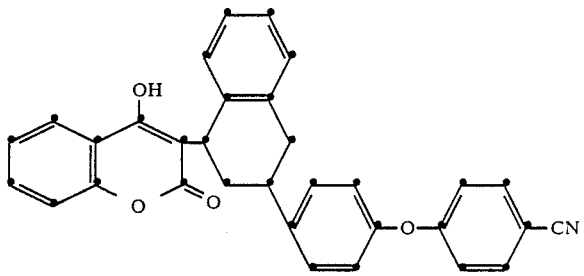

12. A rodenticidal composition comprising a carrier in combination with, as active ingredient, a rodenticidally effective amount of a compound according to claims 1, 7, 8 or 10.

13. A method of exterminating rodents at a locus, or preventing or reducing loss or deterioration by rodent attack at said locus, by providing at said locus bait comprising a rodenticidal composition, as claimed in claim 12.

* * * * *